United States Patent [19]

Reed et al.

[11] Patent Number: 4,511,405
[45] Date of Patent: Apr. 16, 1985

[54] ANTIFOULANTS FOR THERMAL CRACKING PROCESSES

[76] Inventors: Larry E. Reed; Randall A. Porter; Floyd E. Farha, Jr.; Jack P. Guillory, all of c/o Phillips Petroleum Company, Bartlesville, Okla. 74004

[21] Appl. No.: 499,077

[22] Filed: May 27, 1983

Related U.S. Application Data

[60] Division of Ser. No. 424,889, Sep. 30, 1982, , which is a continuation-in-part of Ser. No. 348,614, Feb. 12, 1982, abandoned.

[51] Int. Cl.³ .............................................. C09D 5/14
[52] U.S. Cl. .................................. 106/15.05; 514/493
[58] Field of Search ........................... 424/288, 296; 106/15.05

[56] References Cited

U.S. PATENT DOCUMENTS

| | | | |
|---|---|---|---|
| 2,063,596 | 12/1936 | Feiler | 196/133 |
| 3,132,085 | 5/1964 | Summers, Jr. | 208/48 |
| 3,170,865 | 2/1965 | Allen et al. | 208/48 |
| 3,287,210 | 11/1966 | Leebrick | 424/288 |
| 3,288,813 | 11/1966 | Kleiman | 424/288 |
| 3,334,119 | 8/1967 | Cohen | 424/288 |
| 3,382,264 | 5/1968 | Leebrick | 424/288 |
| 3,405,054 | 8/1968 | Arkis et al. | 208/48 |
| 3,442,922 | 5/1969 | Langer | 424/296 |
| 3,463,644 | 8/1969 | Hechenbleckner et al. | 424/288 |
| 3,574,781 | 4/1971 | Racine et al. | 260/683 |
| 3,827,967 | 8/1974 | Nap et al. | 208/48 R |
| 4,097,544 | 6/1978 | Hengstebeck | 260/683 R |
| 4,105,540 | 8/1978 | Weinland | 208/48 AA |
| 4,151,217 | 4/1979 | Amano et al. | 260/683 R |

*Primary Examiner*—John Kight
*Assistant Examiner*—Garnette D. Draper

[57] ABSTRACT

The formation of carbon on metals exposed to hydrocarbons in a thermal cracking process is reduced by contacting such metals with an antifoulant selected from the group consisting of tin, a combination of tin and antimony, a combination of germanium and antimony, a combination of tin and germanium and a combination of tin, antimony and germanium.

6 Claims, 4 Drawing Figures

ANTIFOULANTS FOR THERMAL CRACKING PROCESSES

This application is a divisional of application Ser. No. 424,889, filed Sept. 30, 1982, which is a continuation-in-part of application Ser. No. 348,614, filed Feb. 12, 1982, now abandoned.

This invention relates to processes for the thermal cracking of a gaseous stream containing hydrocarbons. In one aspect this invention relates to a method for reducing the formation of carbon on the cracking tubes in furnaces used for the thermal cracking of a gaseous stream containing hydrocarbons and in any heat exchangers used to cool the effluent flowing from the furnaces. In another aspect this invention relates to particular antifoulants which are useful for reducing the rate of formation of carbon on the walls of such cracking tubes and in such heat exchangers.

The cracking furnace forms the heart of many chemical manufacturing processes. Often, the performance of the cracking furnace will carry the burden of the major profit potential of the entire manufacturing process. Thus, it is extremely desirable to maximize the performance of the cracking furnace.

In a manufacturing process such as the manufacture of ethylene, feed gas such as ethane and/or propane and/or naphtha is fed into the cracking furnace. A diluent fluid such as steam is usually combined with the feed material being provided to the cracking furnace. Within the furnace, the feed stream which has been combined with the diluent fluid is converted to a gaseous mixture which primarily contains hydrogen, methane, ethylene, propylene, butadiene, and small amounts of heavier gases. At the furnace exit this mixture is cooled, which allows removal of most of the heavier gases, and compressed.

The compressed mixture is routed through various distillation columns where the individual components such as ethylene are purified and separated. The separated products, of which ethylene is the major product, then leave the ethylene plant to be used in numerous other processes for the manufacture of a wide variety of secondary products.

The primary function of the cracking furnace is to convert the feed stream to ethylene and/or propylene. A semi-pure carbon which is termed "coke" is formed in the cracking furnace as a result of the furnace cracking operation. Coke is also formed in the heat exchangers used to cool the gaseous mixture flowing from the cracking furnace. Coke formation generally results from a combination of a homogeneous thermal reaction in the gas phase (thermal coking) and a heterogeneous catalytic reaction between the hydrocarbon in the gas phase and the metals in the walls of the cracking tubes or heat exchangers (catalytic coking).

Coke is generally referred to as forming on the metal surfaces of the cracking tubes which are contacted with the feed stream and on the metal surfaces of the heat exchangers which are contacted with the gaseous effluent from the cracking furnace. However, it should be recognized that coke may form on connecting conduits and other metal surfaces which are exposed to hydrocarbons at high temperatures. Thus, the term "Metals" will be used hereinafter to refer to all metal surfaces in a cracking process which are exposed to hydrocarbons and which are subject to coke deposition.

A normal operating procedure for a cracking furnace is to periodically shut down the furnace in order to burn out the deposits of coke. This downtime results in a substantial loss of production. In addition, coke is an excellent thermal insulator. Thus, as coke is deposited, higher furnace temperatures are required to maintain the gas temperature in the cracking zone at a desired level. Such higher temperatures increase fuel consumption and will eventually result in shorter tube life.

Another problem associated with carbon formation is erosion of the Metals, which occurs in two fashions. First, it is well known that in the formation of catalytic coke the metal catalyst particle is removed or displaced from the surface and entrained within the coke. This phenomenon results in extremely rapid metal loss and, ultimately, Metals failure. A second type of erosion is caused by carbon particles that are dislodged from the tube walls and enter the gas stream. The abrasive action of these particles can be particularly severe on the return bends in the furnace tube.

Yet another and more subtle effect of coke formation occurs when coke enters the furnace tube alloy in the form of a solid solution. The carbon then reacts with the chromium in the alloy and chromium carbide precipitates. This phenomena, known as carburization, causes the alloy to lose its original oxidation resistance, thereby becoming susceptible to chemical attack. The mechanical properties of the tube are also adversely affected. Carburization may also occur with respect to iron and nickel in the alloys.

It is thus an object of this invention to provide a method for reducing the formation of coke on the Metals. It is another object of this invention to provide particular antifoulants which are useful for reducing the formation of carbon on the Metals.

In accordance with the present invention, an antifoulant selected from the group consisting of tin, a combination of tin and antimony, a combination of germanium and antimony, a combination of tin and germanium and a combination of tin, antimony and germanium is contacted with the Metals either by pretreating the Metals with the antifoulant, adding the antifoulant to the hydrocarbon feedstock flowing to the cracking furnace or both. The use of the antifoulant substantially reduces the formation of coke on the Metals which substantially reduces the adverse consequences which attend such coke formation.

Other objects and advantages of the invention will be apparent from the foregoing brief description of the invention and the claims as well as the detailed description of the drawings in which:

The invention is described in terms of a cracking furnace used in a process for the manufacture of ethylene. However, the applicability of the invention described herein extends to other processes wherein a cracking furnace is utilized to crack a feed material into some desired components and the formation of coke on the walls of the cracking tubes in the cracking furnace or other metal surfaces associated with the cracking process is a problem.

Any suitable form of germanium may be utilized in the combination of germanium and antimony antifoulant, in the combination of tin and germanium antifoulant or in the combination of tin, antimony and germanium antifoulant. Elemental germanium, inorganic compounds and organic germanium compounds as well as mixtures of any two or more thereof are suitable sources of germanium. The term "germanium" generally refers to any one of these germanium sources.

Examples of some inorganic germanium compounds that can be used include the halides, nitrides, hydrides, oxides, sulfides, imides, sulfates, and phosphates. Of the inorganic germanium compounds, those which do not contain halogen are preferred.

Examples of organic germanium compounds that can be used include compounds of the formula wherein $R_1$, $R_2$, $R_3$, and $R_4$ are selected independently from the group consisting of hydrogen, halogen, hydrocarbyl, and oxyhydrocarbyl. The hydrocarbyl and oxyhydrocarbyl radicals can have from 1-20 carbon atoms which may be substituted with halogen, nitrogen, phosphorus, or sulfur. Exemplary hydrocarbyl radicals are alkyl, alkenyl, cycloalkyl, aryl, and combinations thereof, such as alkylaryl or alkycycloalkyl. Germanium compounds such as tetrabutylgermanium, germanium tetraethoxide, tetraphenylgermanium, germanium tetraphenoxide, and diphenyldibromogermanium can be employed. At present germanium tetraethoxide is preferred.

Any suitable form of antimony may be utilized in the combination of tin and antimony antifoulant, in the combination of germanium and antimony antifoulant or in the combination of tin, antimony and germanium antifoulant. Elemental antimony, inorganic antimony compounds and organic antimony compounds as well as mixtures of any two or more thereof are suitable sources of antimony. The term "antimony" generally refers to any one of these antimony sources.

Examples of some inorganic antimony compounds which can be used include antimony oxides such as antimony trioxide, antimony tetroxide, and antimony pentoxide; antimony sulfides such as antimony trisulfide and antimony pentasulfide; antimony sulfates such as antimony trisulfate; antimonic acids such as metaantimonic acid, orthoantimonic acid and pyroantimonic acid; antimony halides such as antimony trifluoride, antimony trichloride, antimony tribromide, antimony triiodide, antimony pentafluoride and antimony pentachloride; antimonyl halides such as antimonyl chloride and antimonyl trichloride. Of the inorganic antimony compounds, those which do not contain halogen are preferred.

Examples of some organic antimony compounds which can be used include antimony carboxylates such as antimony triformate, antimony trioctoate, antimony triacetate, antimony tridodecanoate, antimony trioctadecanoate, antimony tribenzoate, and antimony tris(-cyclohexenecarboxylate); antimony thiocarboxylates such as antimony tris(thioacetate), antimony tris(dithioacetate) and antimony tris(dithiopentanoate); antimony thiocarbonates such as antimony tris(O-propyl dithiocarbonate); antimony carbonates such as antimony tris(ethyl carbonates); trihydrocarbylantimony compounds such as triphenylantimony; trihydrocarbylantimony oxides such as triphenylantimony oxide; antimony salts of phenolic compounds such as antimony triphenoxide; antimony salts of thiophenolic compounds such as antimony tris(-thiophenoxide); antimony sulfonates such as antimony tris(benzenesulfonate) and antimony tris(p-toluenesulfonate); antimony carbamates such as antimony tris(diethylcarbamate); antimony thiocarbamates such as antimony tris(dipropyldithiocarbamate), antimony tris(-phenyldithiocarbamate) and antimony tris(butylthiocarbamate); antimony phosphites such as antimony tris(-diphenyl phosphite); antimony phosphates such as antimony tris(-dipropyl)phosphate; antimony thiophosphates such as antimony tris(O,O-dipropyl thiophosphate) and antimony tris(O,O-dipropyl dithiophosphate) and the like. At present antimony 2-ethylhexanoate is preferred.

Any suitable form of tin may be utilized as the tin antifoulant, in the combination of tin and antimony antifoulant, in the combination of tin and germanium antifoulant or in the combination of tin, antimony and germanium antifoulant. Elemental tin, inorganic tin compounds, and organic tin compounds as well as mixtures of any two or more thereof are suitable sources of tin. The term "tin" generally refers to any one of these tin sources.

Examples of some inorganic tin compounds which can be used include tin oxides such as stannous oxide and stannic oxide; tin sulfides such as stannous sulfide and stannic sulfide; tin sulfates such as stannous sulfate and stannic sulfate; stannic acids such as metastannic acid and thiostannic acid; tin halides such as stannous fluoride, stannous chloride, stannous bromide, stannous iodide, stannic fluoride, stannic chloride, stannic bromide and stannic iodide; tin phosphates such as stannic phosphate; tin oxyhalides such as stannous oxychloride and stannic oxychloride; and the like. Of the inorganic tin compounds those which do not contain halogen are preferred as the source of tin.

Examples of some organic tin compounds which can be used include tin carboxylates such as stannous formate, stannous acetate, stannous butyrate, stannous octoate, stannous decanoate, stannous oxalate, stannous benzoate, and stannous cyclohexanecarboxylate; tin thiocarboxylates such as stannous thioacetate and stannous dithioacetate; dihydrocarbyltin bis(hydrocarbyl mercaptoalkanoates) such as dibutyltin bis(isooctyl mercaptoacetate) and dipropyltin bis(butyl mercaptoacetate); tin thiocarbonates such as stannous O-ethyl dithiocarbonate; tin carbonates such as stannous propyl carbonate; tetrahydrocarbyltin compounds such as tetrabutyltin, tetraoctyltin, tetradodecyltin, and tetraphenyltin; dihydrocarbyltin oxides such as dipropyltin oxide, dibutyltin oxide, dioctyltin oxide, and diphenyltin oxide; dihydrocarbyltin bis(hydrocarbyl mercaptide)s such as dibutyltin bis(dodecyl mercaptide); tin salts of phenolic compounds such as stannous thiophenoxide; tin sulfonates such as stannous benzenesulfonate and stannous-p-toluenesulfonate; tin carbamates such as stannous diethylcarbamate; tin thiocarbamates such as stannous propylthiocarbamate and stannous diethyldithiocarbamate; tin phosphites such as stannous diphenyl phosphite; tin phosphates such as stannous dipropyl phosphate; tin thiophosphates such as stannous O,O-dipropyl thiophosphate, stannous O,O-dipropyl dithiophosphate and stannic O,O-dipropyl dithiophosphate, dihydrocarbyltin bis(O,O-dihydrocarbyl thiophosphate)s such as dibutyltin bis(O,O-dipropyl dithiophosphate); and the like. At present stannous 2-ethylhexanoate is preferred.

Any of the listed sources of tin may be combined with any of the listed sources of antimony or germanium to form the combination of tin and antimony antifoulant, the combination of tin and germanium antifoulant or the combination of tin, antimony and germanium antifoulant. In like manner, any of the listed sources of germanium may be combined with any of the listed sources of antimony to form the combination of germanium and antimony antifoulant.

Any suitable concentration of antimony in the combination of tin and antimony antifoulant may be utilized. A concentration of antimony in the range of about 10 mole percent to about 75 mole percent is presently preferred because the effect of the combination of tin and antimony antifoulant is reduced outside of this range. In like manner, any suitable concentration of antimony may be utilized in the combination of germanium and antimony antifoulant. A concentration of antimony in the range of about 10 mole percent to about 75 mole percent is presently preferred because the effect of the combination of germanium and antimony antifoulant is reduced outside of this range.

Any suitable concentration of germanium may be utilized in the combination of tin and germanium antifoulant. A concentration of germanium in the range of about 10 mole percent to about 75 mole percent is presently preferred because it is believed that the effect of the combination of tin and germanium antifoulant would be reduced outside this range.

Any suitable concentration of antimony in the combination of tin, antimony and germanium may be utilized. A concentration in the range of about 10 mole percent to about 65 mole percent is presently preferred. In like manner, a concentration of germanium in the range of about 10 mole percent to about 65 mole percent is presently preferred.

In general, the combination antifoulants of the present invention are effective to reduce the buildup of coke on any of the high temperature steels. The tin antifoulant is considered to be effective to reduce the buildup of coke on any of the high temperature steels other than steels having an iron content of about 98 weight percent or higher. Commonly used steels in cracking tubes are Incoloy 800, Inconel 600, HK40, 1¼ chromium-½ molybdenum steel, and Type 304 Stainless Steel. The composition of these steels in weight percent is as follows:

If the Metals are to be pretreated, a preferred pretreatment method is to contact the Metals with a solution of the antifoulant. The cracking tubes are preferably flooded with the antifoulant. The antifoulant is allowed to remain in contact with the surface of the cracking tubes for any suitable length of time. A time of at least about one minute is preferred to insure that all of the surface of the cracking tube has been treated. The contact time would typically be about ten minutes or longer in a commercial operation. However, it is not believed that the longer times are of any substantial benefit other than to fully assure an operator that the cracking tube has been treated.

It is typically necessary to spray or brush the antifoulant solution on the Metals to be treated other than the cracking tubes but flooding can be used if the equipment can be subjected to flooding.

Any suitable solvent may be utilized to prepare the solution of antifoulant. Suitable solvents include water, oxygen-containing organic liquids such as alcohols, ketones and esters and aliphatic and aromatic hydrocarbons and their derivatives. The presently preferred solvents are normal hexane and toluene although kerosene would be a typically used solvent in a commercial operation.

Any suitable concentration of the antifoulant in the solution may be utilized. It is desirable to use a concentration of at least 0.1 molar and concentrations may be 1 molar or higher with the strength of the concentrations being limited by metallurgical and economic considerations. The presently preferred concentration of antifoulant in the solution is in the range of about 0.2 molar to about 0.5 molar.

Solutions of antifoulants can also be applied to the surfaces of the cracking tube by spraying or brushing when the surfaces are accessible but application in this manner has been found to provide less protection against coke deposition than immersion. The cracking tubes can also be treated with finely divided powders of the antifoulants but, again, this method is not considered to be particularly effective.

In addition to pretreating of the Metals with the antifoulant or as an alternate method of contacting the Metals with the antifoulant, any suitable concentration of the antifoulant may be added to the feed stream flowing through the cracking tube. A concentration of antifoulant in the feed stream of at least ten parts per million by weight of the metal(s) contained in the antifoulant based on the weight of the hydrocarbon portion of the feed stream should be used. Presently preferred concentrations of antifoulant metals in the feed stream are in the range of about 20 parts per million to about

| STEEL | Ni | Cu | C | Fe | S | Cr | Mo | P | Mn | Si |
|---|---|---|---|---|---|---|---|---|---|---|
| Inconel 600 | 72 | .5 | .15 | 8.0 | | 15.5 | | | | |
| Incoloy 800 | 32.5 | .75 | .10 | 45.6 | | 21.0 | | 0.04 max | | |
| HK-40 | 19.0–22.0 | | 0.35–0.45 | balance ≅50 | 0.40 max | 23.0–27.0 | | | 1.5 max | 1.75 max |
| 1¼Cr—½Mo | | | | balance ≅98 | 0.40 max | 0.99–1.46 | 0.40–0.65 | 0.035 max | 0.36–0.69 | 0.13–0.32 |
| 304SS | 9.0 | | 0.8 | 72 | | 19 | | | | |

The antifoulants of the present invention may be contacted with the Metals either by pretreating the Metals with the antifoulant, adding the antifoulant to the hydrocarbon containing feedstock or preferably both.

100 parts per million based on the weight of the hydrocarbon portion of the feed stream. Higher concentrations of the antifoulant may be added to the feed stream but the effectiveness of the antifoulant does not substantially increase and economic considerations generally preclude the use of higher concentrations.

The antifoulant may be added to the feed stream in any suitable manner. Preferably, the addition of the antifoulant is made under conditions whereby the antifoulant becomes highly dispersed. Preferably, the antifoulant is injected in solution through an orifice under pressure to atomize the solution. The solvents previously discussed may be utilized to form the solutions. The concentration of the antifoulant in the solution should be such as to provide the desired concentration of antifoulant in the feed stream.

Steam is generally utilized as a diluent for the hydrocarbon containing feedstock flowing to the cracking furnace. The steam/hydrocarbon molar ratio should not be allowed to exceed 2:1 when the tin antifoulant of the present invention is being used since the effectiveness of the tin antifoulant is substantially reduced at steam/hydrocarbon molar ratios above 2:1. The preferred steam/hydrocarbon molar ratio is in the range of about 0.25:1 to about 0.75:1 to enhance the effectiveness of the tin antifoulant.

The steam/hydrocarbon molar ratio is considered to have very little effect on the use of the combination of tin and antimony antifoulant, the combination of germanium and antimony antifoulant, the combination of germanium and tin antifoulant or the combination of tin, antimony and germanium antifoulant. It is believed that the steam/hydrocarbon molar ratio is critical for tin alone because the tin antifoulant is volatile at high steam/hydrocarbon molar ratios. The combination antifoulants do not seem to exhibit this same volatility.

The cracking furnace may be operated at any suitable temperature and pressure. In the process of steam cracking of light hydrocarbons to ethylene, the temperature of the fluid flowing through the cracking tubes increases during its transit through the tubes and will attain a maximum temperature at the exit of the cracking furnace of about 850° C. The wall temperature of the cracking tubes will be higher and may be substantially higher as an insulating layer of coke accumulates within the tubes. Furnace temperatures of nearly 2000° C. may be employed. Typical pressures for a cracking operation will generally be in the range of about 10 to about 20 psig at the outlet of the cracking tube.

Figure 1:
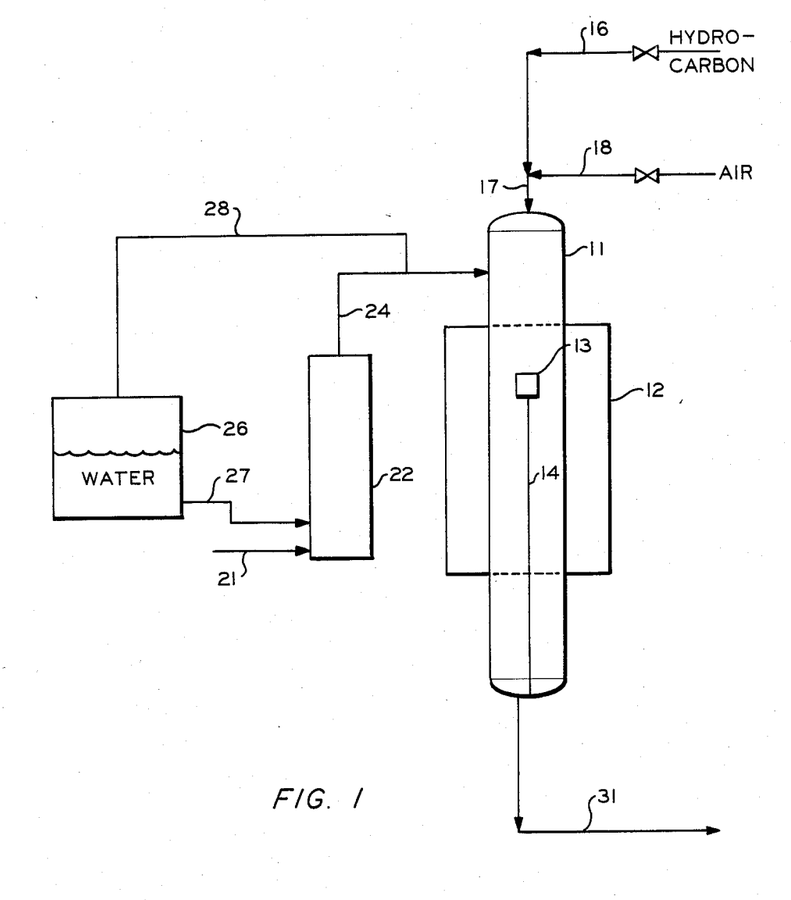
FIG. 1 is a diagrammatic illustration of the test apparatus used to test the antifoulants of the present invention.

Before referring specifically to the examples which will be utilized to further illustrate the present invention, the laboratory apparatus will be described by referring to FIG. 1 in which a 9 millimeter quartz reactor 11 is illustrated. A part of the quartz reactor 11 is located inside the electric furnace 12. A metal coupon 13 is supported inside the reactor 11 on a two millimeter quartz rod 14 so as to provide only a minimal restriction to the flow of gases through the reactor 11. A hydrocarbon feed stream (ethylene) is provided to the reactor 11 through the combination of conduit means 16 and 17. Air is provided to the reactor 11 through the combination of conduit means 18 and 17.

Nitrogen flowing through conduit means 21 is passed through a heated saturator 22 and is provided through conduit means 24 to the reactor 11. Water is provided to the saturator 22 from the tank 26 through conduit means 27. Conduit means 28 is utilized for pressure equalization.

Steam is generated by saturating the nitrogen carrier gas flowing through the saturator 22. The steam/nitrogen ratio is varied by adjusting the temperature of the electrically heated saturator 22.

The reaction effluent is withdrawn from the reactor 11 through conduit means 31. Provision is made for diverting the reaction effluent to a gas chromatograph as desired for analysis.

In determining the rate of coke deposition on the metal coupon, the quantity of carbon monoxide produced during the cracking process was considered to be proportional to the quantity of coke deposited on the metal coupon. The rationale for this method of evaluating the effectiveness of the antifoulants was the assumption that carbon monoxide was produced from deposited coke by the carbon-steam reaction. Metal coupons examined at the conclusion of cracking runs bore essentially no free carbon which supports the assumption that the coke had been gasified with steam.

The selectivity of the converted ethylene to carbon monoxide was calculated according to equation 1 in which nitrogen was used as an internal standard.

$$\% \text{ Selectivity (CO)} = \frac{(\text{mole } \% \text{ CO/mole } \% \text{ N}_2) \times 100}{\text{Conversion}} \quad (1)$$

The conversion was calculated according to equation 2.

$$\text{Conversion} = \frac{(\text{mole } \% \text{ C}_2\text{H}_4/\text{mole } \% \text{ N}_2)_{Feed} - (\text{mole } \% \text{ C}_2\text{H}_4/\text{mole } \% \text{ N}_2)_{sample}}{(\text{mole } \% \text{ C}_2\text{H}_4/\text{mole } \% \text{ N}_2)_{Feed}} \quad (2)$$

The CO level for the entire cycle was calculated as a weighted average of all the analyses taken during a cycle according to equation 3.

$$\text{Time Weighted Selectivity} = \frac{\Sigma \text{Selectivity} \times \text{Time}^{\frac{1}{2}}}{\Sigma \text{Time}^{\frac{1}{2}}} \quad (3)$$

The percent selectivity is directly related to the quantity of carbon monoxide in the effluent flowing from the reactor.

EXAMPLE 1

Incoloy 800 coupons, $1'' \times \frac{1}{4}'' \times 1/16''$, were employed in this example. Prior to the application of a coating, each Incoloy 800 coupon was thoroughly cleaned with acetone. Each antifoulant was then applied by immersing the coupon in a minimum of 4 mL of the antifoulant/solvent solution for 1 minute. A new coupon was used for each antifoulant. The coating was then followed by heat treatment in air at 700° C. for 1 minute to decompose the antifoulant to its oxide and to remove any residual solvent. A blank coupon, used for comparisons, was prepared by washing the coupon in acetone and heat treating in air at 700° C. for 1 minute without any coating. The preparation of the various coatings are given below.

0.5M Sb: 2.76 g of $Sb(C_8H_{15}O_2)_3$ was mixed with enough pure n-hexane to make 10.0 mL of solution referred to hereinafter as solution A.

0.5M Ge: 1.26 g $Ge(OC_2H_5)_4$ was dissolved in enough absolute ethanol to make 10.0 mL of solution referred to hereinafter as solution B.

0.5M Sn: 2.02 g of $Sn(C_8H_{15}O_2)_2$ was dissolved in enough pure n-hexane to make 10.0 mL of solution referred to hereinafter as solution C.

0.5M Sn-Sb: 0.81 g of $Sn(C_8H_{15}O_2)_2$ was dissolved in enough pure grade n-hexane to make 4.0 mL of solution. The antimony solution was prepared by dissolving 1.10 g of $Sb(C_8H_{15}O_2)_3$ in enough pure n-hexane to make 4 mL. The two solutions were combined and mixed thoroughly and the resulting mixture is referred to hereinafter as solution D.

0.5M Ge-Sb: 5.0 g of $Ge(OC_2H_5)_4$ was dissolved in enough absolute ethanol to make 40.0 mL. Then 1.1 g of $Sb(C_8H_{15}O_2)_3$ was dissolved in enough pure n-hexane to make 4.0 mL. The 1:1 Ge-Sb solution was prepared by mixing 4.0 mL of each solution together and is referred to hereinafter as solution E.

0.5M Ge-Sn: 1.26 g $Ge(OC_2H_5)_4$ was dissolved in absolute ethanol and diluted with alcohol to exactly 10 mL. 2.7 g $Sn(C_8H_{15}O_2)_3$, was dissolved in pure n-hexane and diluted with n-hexane to exactly 10 mL. The two solutions were combined and mixed and are referred to hereinafter as solution F.

0.1M Sn-Sb: A 2.0 mL aliquot of solution D was added to a graduated cylinder and enough toluene was added to make 10.0 mL. The resulting solution is referred to hereinafter as solution G.

0.1M Sn-Sb-Ge: 0.68 g of $Sn(C_8H_{15}O_2)_2$, 0.92 g of $Sb(C_8H_{15}O_2)_3$ and 0.42 g of $Ge(OC_2H_5)_4$ were dissolved in enough toluene to make 10.0 mL. A 2.0 mL aliquot of this solution was added to a graduated cylinder and enough toluene was added to make 10.0 mL. The resulting solution is referred to hereinafter as solution H.

The temperature of the quartz reactor was maintained so that the hottest zone was 900°±5° C. A coupon was placed in the reactor while the reactor was at reaction temperature.

A typical run consisted of three 20 hour coking cycles (ethylene, nitrogen and steam), each of which was followed by a 5 minute nitrogen purge and a 50 minute decoking cycle (nitrogen, steam and air). During a coking cycle, a gas mixture consisting of 73 mL per minute ethylene, 145 mL per minute nitrogen and 73 mL per minute steam passed downflow through the reactor. Periodically, snap samples of the reactor effluent were analyzed in a gas chromatograph. The steam/hydrocarbon molar ratio was 1:1.

Table I summarizes results of cyclic runs (with either 2 or 3 cycles) made with Incoloy 800 coupons that had been immersed in the test solutions A-H previously described.

TABLE I

| Run | Solution | Time Weighted Selectivity to CO | | |
| | | Cycle 1 | Cycle 2 | Cycle 3 |
| --- | --- | --- | --- | --- |
| 1 | None (Control) | 19.9 | 21.5 | 24.2 |
| 2 | A | 15.6 | 18.3 | — |
| 3 | B | 18.5 | 30.4 | — |
| 4 | C | 5.6 | 8.8 | 21.6 |
| 5 | D | 0.74 | 2.2 | 4.9 |
| 6 | E | 1.5 | 5.0 | — |
| 7 | F | 10.9 | 19.1 | 20.5 |
| 8 | F | 4.2 | 8.9 | 15.1 |
| 9 | F | 3.1 | 9.1 | 18.7 |
| 10 | G | 5.8 | 9.9 | 16.2 |
| 11 | H | 2.9 | 8.7 | 15.8 |
| 12 | H | 2.8 | 5.0 | — |

Results of runs 2, 3, and 4 in which tin, antimony and germanium were used separately, show that only tin was effective in substantially reducing the rate of carbon deposition on Incoloy 800 under conditions simulating those in an ethane cracking process. However, binary combinations of these elements used in runs 5, 6, 7, 8 and 9 show some very surprising effects. Run 5, in which tin and antimony were combined, and run 6, in which germanium and antimony were combined, show that these combinations are unexpectedly much more effective than results of runs in which they were used separately would lead one to expect.

Runs 8 and 9 show an improvement over tin alone that is unexpected in view of the effect of germanium alone. However, the combination of tin and germanium antifoulant does not show the dramatic improvement exhibited by the combination of tin and antimony antifoulant and the combination of germanium and antimony antifoulant and thus this antifoulant is not the preferred antifoulant among the combination antifoulants.

It is not known why run 7 was less effective than tin alone. However, runs 8 and 9 are considered to be more exemplary of the effect of the combination of tin and germanium antifoulant and it is believed that this antifoulant is more effective than tin alone.

In runs 10, 11 and 12, 0.1M solutions were used in order to show the improvement provided by the trinary combination. Higher concentrations such as 0.5M have a tendency to mask the improvement. A comparison of runs 10, 11 or 12 shows that the combination of tin, antimony and germanium antifoulant is significantly more effective than the best binary combination (Sn-Sb).

EXAMPLE 2

Using the process conditions of Example 1, a plurality of three cycle runs were made using antifoulants which contained different ratios of tin and antimony and different ratios of germanium and antimony. Each run employed a new Incoloy 800 coupon which had been cleaned and treated as described in Example 1. The antifoulant solutions were prepared as described in Example 1 with the exception that the ratio of the elements was varied. The results of these tests are illustrated in FIGS. 2 and 3.

Figure 2:
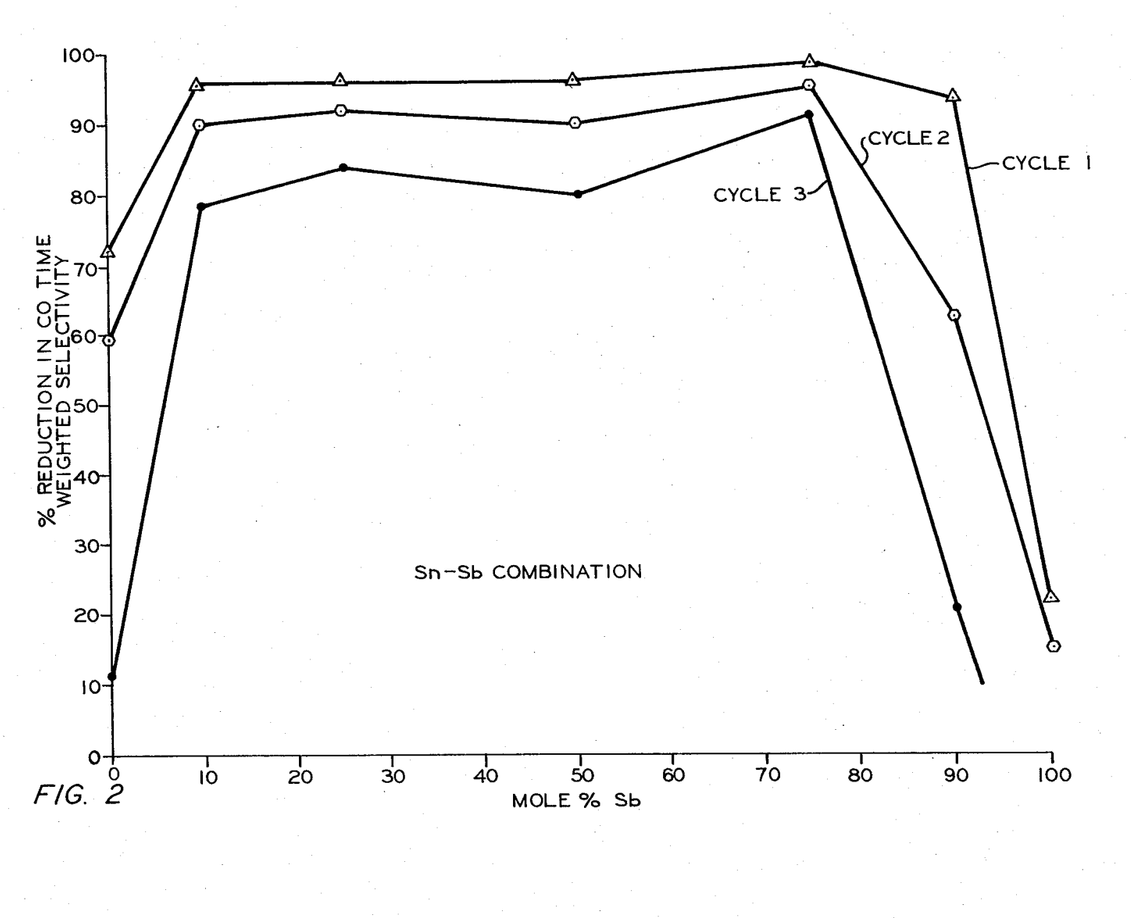
FIG. 2 is a graphical illustration of the effect of a combination of tin and antimony.
Figure 3:
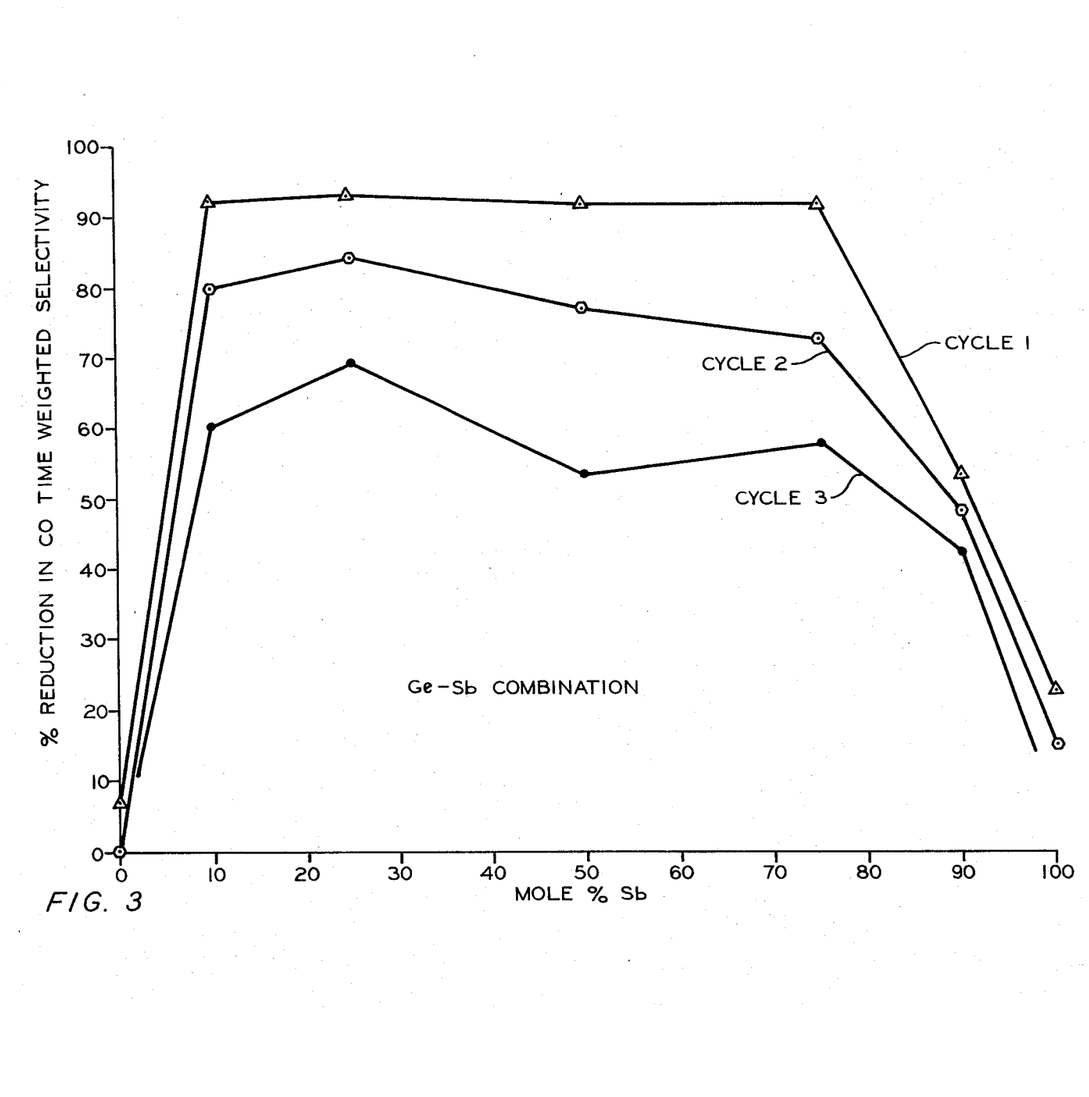
FIG. 3 is a graphical illustration of the effect of a combination of germanium and antimony.

Referring to FIG. 2, it can be seen that the combination of tin and antimony was particularly effective when the concentration of antimony ranged from about 10 mole percent to about 75 mole percent. Outside of this range, the effectiveness of the combination of tin and antimony was reduced particularly in the second and third cycles.

Referring now to FIG. 3, it can again be seen that the combination of germanium and antimony was effective when the concentration of antimony was in the range of about 10 mole percent to about 75 mole percent. Again, the effectiveness of the combination of germanium and antimony is reduced outside of this range. Also, it can be noted that the effectiveness of the combination of germanium and antimony is reduced more each cycle than was seen in the combination of tin and antimony.

It is believed that the combination of tin and germanium antifoulant would act essentially the same as the combination of tin and antimony antifoulant with respect to effectiveness as a function of concentration and thus a concentration of germanium in the combination of tin and germanium antifoulant is preferably in the range of about 10 mole percent to about 75 mole percent.

EXAMPLE 3

Coupons of 1¼ chromium-½ molybdenum steel alloy, which is the alloy commonly used in transfer line heat exchangers in commercial ethylene cracking units, were cleaned in the manner described in Example 1. Separate coupons were then treated with solutions A, C or D of Example 1. Each coupon, including a control coupon, was then subjected to cyclic runs under the conditions set forth in Example 1. The results are summarized in Table II. Because of experimental difficulties associated with analysis of effluent gases, the reported observations are at different times but are nevertheless considered to provide a comparison of the effectiveness of the antifoulants.

TABLE II

| Treating Agent | Time, Hr. | $C_2H_4$ Conv., % | Sel. to CO, % |
|---|---|---|---|
| None* | 2 | 13.8 | 43.6 |
|  | 4 | 19.1 | 70.8 |
|  | 6 | 23.3 | 83.5 |
|  | 8 | 24.2 | 86.5 |
| Sn | 24 | 31.2 | 82.6 |
|  | 30 | 25.6 | 82.1 |
|  | 36 | 23.6 | 82.4 |
|  | 53 | 45.5 | 97.1 |
| Sb | 5 | 42.0 | 86.5 |
| Sn + Sb | 2 | 14.0 | 2.5 |
|  | 4 | 13.8 | 1.6 |
|  | 6 | 13.8 | 1.8 |
|  | 8 | 13.9 | 1.8 |
|  | 12 | 14.5 | 4.1 |
|  | 16 | 14.6 | 2.8 |
|  | 20 | 15.4 | 5.4 |
|  | 23 | 15.6 | 7.8 |

*Run continued for 21.2 hours but no other analyses were obtained because of instrumental difficulties. In its second cycle the run was terminated after 1.2 hours because sufficient carbon to totally obstruct flow collected on the coupon.

Treatment of 1¼Cr-½Mo steel alloy with solutions of tin or antimony separately is considered to be ineffective to reduce the rate of carbon deposition under the conditions of these runs. However, when both tin and antimony are present, the rate of carbon deposition at the same conditions was decreased substantially.

EXAMPLE 4

Coupons of Type 304 Stainless Steel were cleaned in the manner described in Example 1. A coupon was then treated with solution C of Example 1. The treated coupon and a control coupon were then subjected to a cyclic run under the conditions set forth in Example 1. The results are summarized in Table III.

TABLE III

| Treating Agent | Time Weighted Selectivity to CO | | |
|---|---|---|---|
|  | Cycle 1 | Cycle 2 | Cycle 3 |
| None | 23.3 | 74.2 | 85.4 |
| Sn | 4.1 | 6.0 | 8.1 |

Table III illustrates that tin is an effective antifoulant for Type 304 Stainless Steel which has an iron content of about 72 weight percent. In contrast, Example 3 demonstrates that tin is not an effectie antifoulant for 1¼Cr-½Mo steel alloy which has an iron content of about 98 weight percent. It is thus believed that tin is an effective antifoulant for steels having relatively high iron contents but the use of tin on steels having a iron content of about 98 weight percent or higher should be avoided.

EXAMPLE 5

The tin antifoulant of the present invention was used in tests on a commercial ethylene cracking furnace. The feedstock for the cracking furnace was ethane with the exception of a few relatively short intervals when propane was used. The cracking tubes were separated from the downstream transfer line heat exchanger and a solution containing stannous octoate was pumped into the cracking tubes to fill the tubes. The treating solution was prepared by diluting stannous octoate, catalyst T-9 from M & T Chemicals, Inc., with ten volumes of kerosene. The undiluted compound is reported by the manufacturer to contain typically 28 weight percent tin.

After approximately ten minutes, the solution of stannous octoate was drained from the cracking tubes. In addition to treating the tubes, the solution of stannous octoate was also applied by spraying to the transfer line heat exchanger.

Operation of a cracking furnace is terminated when the inlet pressure to the cracking tubes exceeds a predetermined limit. When the predetermined limit is exceeded, the cracking furnace is shut down for oxidative burn-out to remove the coke obstruction. In the cracking furnace in which the tests were made, the tubes had operated without antifoulant from ten to thirty-one days and had been then subjected to an oxidative burn-out to remove coke. In three separate tests made with a treatment of antifoulant as previously described, operation was maintained for 40, 49 and 47 days which is a substantial improvement over the 31-day maximum seen without the antifoulant treatment.

One run was made in which, in addition to treating the tubes of the cracking furnace and the transfer line exchanger as previously described, the solution of stannous octoate was injected into the ethane before the ethane entered the cracking furnace. The concentration of tin in the ethane was 23 parts per million. The antifoulant solution was dispersed in the ethane by being forced through an orifice at elevated pressure into the stream of ethane which was moving with a linear velocity of about 1000 feet per second. Injection of the antifoulant solution was continued for 10 of the first 11 days of operation and then terminated.

In this run, the cracking tube was in use for 60 days before excessive inlet pressure necessitated its shutdown.

All operations in the commercial cracking furnace were made at a steam/ethane weight ratio of 0.35:1 and a temperature at the exit of the cracking tube of about 843° C.

EXAMPLE 6

Using the procedure of Example 1 and solution C of Example 1, three separate runs were made at a steam/hydrocarbon molar ratio of 1:1, 2:1 and 2.5:1 respectively. The results of these tests are illustrated in FIG. 4.

Figure 4:
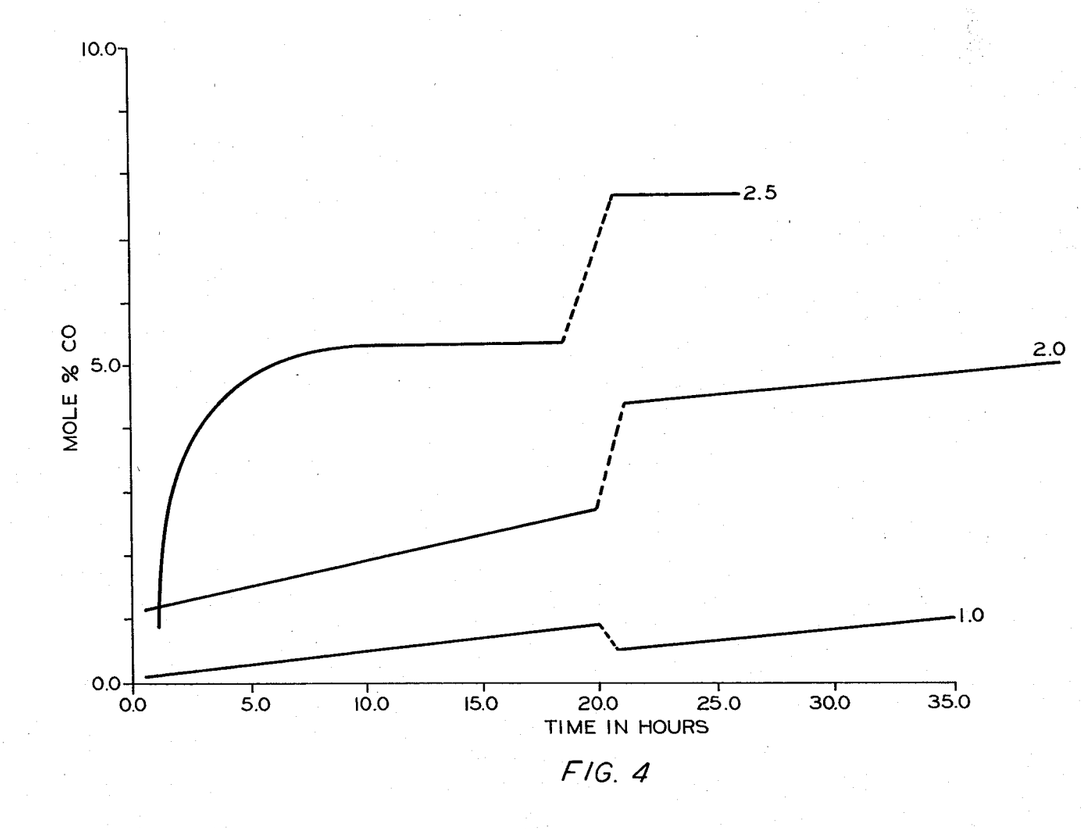
FIG. 4 is a graphical illustration of the effect of steam on the tin antifoulant.

Referring to FIG. 4, it can be seen that the tin antifoulant performed well at a steam/hydrocarbon molar ratio of 1.0. However, the effectiveness decreased at higher steam/hydrocarbon molar ratios.

Reasonable variations and modifications are possible by those skilled in the art within the scope of the described invention and the appended claims.

That which is claimed is:

1. "An antifoulant composition comprising tin, antimony and germanium", wherein the concentration of antimony in said antifoulant composition is in the range of about 10 mole percent to about 65 mole percent and wherein the concentration of germanium in said antifoulant composition is in the range of about 10 mole percent to about 65 mole percent.

2. A composition in accordance with claim 1 wherein said antifoulant composition is in a solution and wherein the concentration of said antifoulant composition in said solution is at least about 0.1 molar.

3. A composition in accordance with claim 2 wherein the concentration of said antifoulant composition in said solution is in the range of about 0.2 molar to about 0.5 molar.

4. A composition in accordance with claim 2 wherein the solvent used to form the solution of said antifoulant composition is selected from the group consisting of water, oxygen-containing organic liquids and aliphatic and aromatic hydrocarbons.

5. A composition in accordance with claim 1 wherein said tin is contained in an organic compound of tin, wherein said antimony is contained in an organic compound of antimony and wherein said germanium is contained in an organic compound of germanium.

6. A composition in accordance with claim 5 wherein said organic compound of tin is stannous 2-ethylhexanoate, wherein said organic compound of antimony is antimony 2-ethylhexanoate and wherein said organic compound of germanium is germanium tetraethoxide.

* * * * *